US010602946B2

(12) United States Patent
Schreck et al.

(10) Patent No.: US 10,602,946 B2
(45) Date of Patent: Mar. 31, 2020

(54) MOBILE CARDIAC MONITORING DEVICE

(71) Applicant: VECTRACOR, INC., Totowa, NJ (US)

(72) Inventors: David M. Schreck, Sparta, NJ (US); Brad S. Schreck, Totowa, NJ (US); Andrew J. Schreck, Watchung, NJ (US); Michael G. Van Laar, Sparta, NJ (US)

(73) Assignee: VectraCor, Inc., Totowa, NJ (US)

( * ) Notice: Subject to any disclaimer, the term of this patent is extended or adjusted under 35 U.S.C. 154(b) by 152 days.

(21) Appl. No.: 14/984,838

(22) Filed: Dec. 30, 2015

(65) Prior Publication Data

US 2017/0188861 A1    Jul. 6, 2017

(51) Int. Cl.
*A61B 5/0404* (2006.01)
*A61B 5/0402* (2006.01)
*A61B 5/00* (2006.01)
*A61B 5/04* (2006.01)
*A61B 5/0452* (2006.01)

(52) U.S. Cl.
CPC .......... *A61B 5/0402* (2013.01); *A61B 5/0002* (2013.01); *A61B 5/0006* (2013.01); *A61B 5/0404* (2013.01); *A61B 5/04012* (2013.01); *A61B 5/04028* (2013.01); *A61B 5/0452* (2013.01); *A61B 5/04017* (2013.01); *A61B 5/742* (2013.01); *A61B 5/746* (2013.01)

(58) Field of Classification Search
CPC .......................... A61B 5/04028; A61B 5/0404
See application file for complete search history.

(56) References Cited

U.S. PATENT DOCUMENTS

| 6,901,285 | B2 | 5/2005 | Schreck | |
|---|---|---|---|---|
| 6,920,349 | B2* | 7/2005 | Schreck | A61B 5/0402 600/509 |
| 9,622,674 | B2* | 4/2017 | Wu | A61B 5/04028 |
| 2003/0216655 | A1* | 11/2003 | Schreck | A61B 5/0402 600/509 |
| 2009/0171227 | A1 | 7/2009 | Dziubinski et al. | |

(Continued)

FOREIGN PATENT DOCUMENTS

EP    2030565 A1    3/2009

OTHER PUBLICATIONS

Mirvis D., et al., "Electrocardiography", Braunwald's Heart Disease, 2008, Chapter 12, pp. 149, 155, Saunders Elsevier.

(Continued)

*Primary Examiner* — George R Evanisko
(74) *Attorney, Agent, or Firm* — McCarter & English, LLP; Beverly W. Lubit

(57) ABSTRACT

A mobile cardiac monitoring device is disclosed. The mobile cardiac monitoring device receives voltage-time measurements of a subset of electrocardiogram (ECG) leads for a user, and derives a full set of ECG leads from the voltage-time measurements of the subset of ECG leads. The mobile cardiac monitoring device calculates a heart rate and monitors the cardiac rhythm of the user based on at least one of the subset of ECG leads and calculates a cardiac electrical biomarker (CEB) based on the derived ECG. The mobile cardiac device detects a trigger condition based on the calculated CEB and transmits an alert in response to detecting the trigger condition.

35 Claims, 8 Drawing Sheets

(56) References Cited

U.S. PATENT DOCUMENTS

| | | |
|---|---|---|
| 2010/0004547 A1 | 1/2010 | Scholz et al. |
| 2011/0105928 A1 | 5/2011 | Bojovic et al. |
| 2011/0270112 A1* | 11/2011 | Manera ............... A61B 5/0404 600/523 |
| 2014/0275928 A1* | 9/2014 | Acquista ............ A61B 5/04085 600/382 |
| 2015/0208943 A1 | 7/2015 | Shenasa et al. |

OTHER PUBLICATIONS

PCT/US2016/066502; International Search Report and Written Opinion; dated Mar. 27, 2017; 14 pages.

PCT/US2016/066502; International Preliminary Report on Patentability; dated Jul. 12, 2018; 13 pages.

Schreck et al, Diagnostic Accuracy of a New Cardiac Electrical . . . vol. 19, No. 2, Oct. 7, 2013 p. 129-144.

* cited by examiner

MOBILE CARDIAC MONITORING DEVICE

FIELD OF THE INVENTION

The described invention relates to a mobile cardiac monitoring device, and more particularly to a mobile device for monitoring cardiac rhythm and a dynamic cardiac electrical biomarker.

BACKGROUND OF THE INVENTION

Coronary heart disease leading to acute coronary syndromes (ACS) is the leading cause of mortality in the United States, and chest pain accounts for more than 8 million emergency room visits annually. However, acute myocardial infarction (AMI) is often misdiagnosed in emergency rooms, and many patients with AMI are discharged from emergency rooms without recognition.

Electrophysiology of the Heart

Transmembrane ionic currents are ultimately responsible for the cardiac potentials that are recorded as an ECG. The ECG is the final outcome of a complex series of physiological and technological processes. Transmembrane ionic currents are generated by ion fluxes across cell membranes and between adjacent cells. These currents are synthesized by cardiac activation and recovery sequences to generate a cardiac electrical field in and around the heart that varies with time during the cardiac cycle. This electrical field passes through numerous other structures, including the lungs, blood and skeletal muscle, that perturb the cardiac electrical field as it passes through them. Braunwald's Heart Disease, 8th Ed., Saunders, Elsevier (2008), Chapter 12, at p. 149. The currents reaching the skin are then detected by electrodes placed in specific locations on the extremities and torso that are configured to produce leads. The outputs of these leads are amplified, filtered, and displayed by various electronic devices to produce an electrocardiographic recording, and diagnostic criteria are applied to these recordings to produce an interpretation.

The Cardiac Dipole

Two point sources of equal strength but of opposite polarity located very near each other, such as a current source and a current sink, can be represented as a current dipole. Thus, activation of a single cardiac fiber can be modeled as a current dipole that moves in the direction of propagation of activation. Such a dipole is fully characterized by three parameters: strength or dipole moment, location and orientation. Dipole moment is proportional to the rate of change of intracellular potential. Likewise, multiple adjacent cardiac fibers are activated in synchrony to produce an activation front, which creates a dipole oriented in the direction of activation. The net effect of all the dipoles in this wave front is a single dipole with a strength and orientation equal to the (vector) sum of all the simultaneously active component dipoles. Id. at 150

A current dipole produces a characteristic potential field with positive potentials projected ahead of it and negative potentials projected behind it. The actual potential recorded at any site within this field is directly proportional to the dipole moment, inversely proportional to the square of the distance from the dipole to the recording site, and directly proportional to the cosine of the angle between the axis of the dipole and a line drawn from the dipole to the recording site. Id. at 150

This relationship between activation direction, orientation of the current dipole, and polarity of potentials describes the fundamental relationship between the polarity of potentials sensed by an electrode and the direction of movement of an activation front, i.e., an electrode senses positive potentials when an activation front is moving toward it and negative potentials when the activation front is moving away from it. Id at 150

Transmission factors are contents of the three-dimensional physical environment (called the volume conductor), which modifies the cardiac electrical field in significant ways. Transmission factors may be grouped into four broad categories.

Cellular factors determine the intensity of current fluxes that result from local transmembrane potential gradients; they include intracellular and extracellular resistances and the concentrations of relevant ions, e.g., the sodium ion. Lower ion concentrations reduce the intensity of current flow and reduce extracellular potentials.

Cardiac factors affect the relationship of one cardiac cell to another. Two major factors are (1) anisotropy, the property of cardiac tissue that results in greater current flow and more rapid propagation along the length of a fiber than across its width; and (2) the presence of connective tissue between cardiac fibers, which disrupts effective electrical coupling of adjacent fibers.

Extracardiac factors encompass all the tissues and structures that lie between the activation region and the body surface, including the ventricular walls, intracardiac and intrathoracic blood, pericardium, lungs, skeletal muscle, subcutaneous fat, and skin. These tissues alter the cardiac field because of differences in the electrical resistivity of adjacent tissues, i.e., the presence of electrical inhomogeneities within the torso.

Other factors include changes in the distance between the heart and the recording electrode, which reduce potential magnitudes in proportion to the square of the distance and the eccentricity of the heart within the chest (meaning it lies closer to the anterior than to the posterior region of the torso, and the right ventricle and anteroseptal aspect of the left ventricle are located closer to the anterior chest wall than other parts of the left ventricle and the atria, which means that electrocardiographic potentials will be higher anteriorly than posteriorly, and waveforms projected from the anterior left ventricle to the chest wall will be greater than those generated by posterior ventricular regions. Id. at 151

The Cardiac Cycle

The heart is a current generator, and its electrical field is well known to be overwhelmingly dipolar.

The term "cardiac cycle" is used to refer to all or any of the electrical and mechanical events related to the coronary blood flow or blood pressure that occur from the beginning of one heartbeat to the beginning of the next. Blood pressure increases and decreases throughout the cardiac cycle. The frequency of the cardiac cycle is the heart rate. Every single 'beat' of the heart involves five major stages: (1) "late diastole," which is when the semilunar valves close, the atrioventricular (AV) valves open and the whole heart is relaxed; (2) "atrial systole," which is when the myocardium of the left and right atria are contracting, AV valves open and blood flows from atrium to ventricle; (3) "isovolumic ventricular contraction," which is when the ventricles begin to contract, AV and semilunar valves close, and there is no change in volume; (4) "ventricular ejection," which is when the ventricles are emptied but still contracting and the semilunar valves are open; and (5) "isovolumic ventricular relaxation," when pressure decreases, no blood is entering the ventricles, the ventricles stop contracting and begin to relax, and the semilunar valves are shut because blood in the aorta is pushing them shut. The cardiac cycle is coordinated by a series of electrical impulses that are produced by specialized heart cells found within the sino-atrial node and the atrioventricular node. The heart is activated and recovers during each cardiac cycle in a characteristic manner determined by the anatomy and physiology of working cardiac muscle and the specialized cardiac conduction systems. P. Libby et al., Eds., Braunwald's Heart Disease, $8^{th}$ Ed., Elsevier, Inc., Philadelphia (2008) at 155.

The normal cardiac cycle begins with spontaneous depolarization of the sinus node, an area of specialized tissue situated in the high right atrium (RA). A wave of electrical depolarization then spreads through the RA and across the inter-atrial septum into the left atrium (LA). Id.

The atria are separated from the ventricles by an electrically inert fibrous ring, so that in the normal heart the only route of transmission of electrical depolarization from atria to ventricles is through the atrioventricular (AV) node. Id. The AV node delays the electrical signal for a short time, and then the wave of depolarization spreads down the interventricular septum (IVS), via the bundle of His and the right and left bundle branches, into the right (RV) and left (LV) ventricles. With normal conduction the two ventricles contract simultaneously. Id.

After complete depolarization of the heart, the myocardium must then repolarize, before it can be ready to depolarize again for the next cardiac cycle.

The Standard 12-lead Electrocardiogram

A standard surface ECG is recorded showing 12 different lead 'directions' from eight independent leads, though only 10 recording electrodes on the skin are required to achieve this. Six of these electrodes are placed on the chest overlying the heart to record the six chest or precordial leads. Four electrodes are placed on the limbs to record the six limb leads. In a standard ECG, it is essential that each of the 10 recording electrodes is placed in its correct position, otherwise the appearance of the ECG will be changed significantly, preventing correct interpretation.

For simple bipolar leads, such as leads I, II and III, the lead vectors are directed from the negative electrode toward the positive one. For the augmented limb and precordial leads, the origin of the lead vector lies at the midpoint of the axis connecting the electrodes that make up the compound electrode, i.e., for lead aVL, the vector points from the midpoint of the axis connecting the right arm and left leg electrodes toward the left arm. For the precordial leads, the lead vector points from the center of the triangle formed by the three standard limb leads to the precordial electrode site.

The limb leads record the ECG in the coronal plane, and so can be used to determine the electrical axis (which is usually measured only in the coronal plane). The limb leads are called leads I, II, Ill, aVR, aVL and aVF. A horizontal line through the heart and directed to the left (exactly in the direction of lead I) is conventionally labelled as the reference point of 0 degrees (0°). The directions from which other leads 'look' at the heart are described in terms of the angle in degrees from this baseline.

The chest leads record the ECG in the transverse or horizontal plane, and are called V1, V2, V3, V4, V5 and V6. Other lead conventions exist and may be used clinically including V7, V8, and V9, which are recorded from the posterior left thorax, and V3R, V4R, V5R, and V6R, which are recorded from the anterior right thorax.

Improved ECG Using a Universal Transformation Matrix

An improved ECG technology to detect myocardial injury uses the mathematical techniques of abstract factor analysis and the simplex optimization algorithm to derive a universal transformation matrix that is applicable to all patients and is independent of time (U.S. Pat. No. 6,901,285, incorporated by reference). This universal transformation matrix is applicable when needed and does not require the acquisition of a complete n-lead ECG for each patient prior to its implementation. In order to do this, one first measures and digitizes the voltage-time data for some set of ECG leads to define an ECG training set. Once the voltage-time data arrays have been acquired, an abstract factor analysis ("AFA") technique is applied to each ECG voltage-time data array in a training set in order to minimize the error in the measured arrays. The final step is then to apply a simplex optimization technique ("SOP") to the training set in order to derive a universal transformation matrix applicable to all patients, and is time independent. This universal transformation matrix can then be applied to a standard measured 3 lead subsystem (the measured I, aVF and V2 leads) to derive the standard 12 lead ECG as well as other systems, and can generate at least 22 leads to enable a more accurate interpretation of cardiac electrical activity. These derived ECG leads account for approximately 99% of the information content when compared to observed lead measurements.

The ECG is the first test in the initial evaluation of chest pain patients, but multiple studies have demonstrated that the ECG has low sensitivity in initially diagnosing AMI.

Cardiac serum markers are an important supplement to the ECG in the assessment and risk stratification in acute myocardial ischemic injury. Serum troponin evaluation has recently become the gold standard for the diagnosis of myocardial necrosis. However, serum troponin results are generally not immediately available, nor are they obtained continuously in real time, and initial treatment protocols typically must be implemented by relying only on the initial patient evaluation and the associated 12-lead ECG interpretation.

Rapid diagnosis of acute myocardial ischemic injury, including AMI, is the key to implementing immediate treatment. For presumed acute coronary syndrome (ACS) patients, the ECG and cardiac serum markers are typically acquired at the time of patient arrival and every several hours thereafter, for up to 24 hours of patient observation to identify the developments of an ACS. The patient may be at risk during the time between these serum markers and ECG acquisitions, especially if the patient has silent ischemic injuries. Furthermore, approximately 95% of patients who visit emergency rooms with chest pains are sent home without treatment. These patients may also be at risk.

BRIEF SUMMARY OF THE INVENTION

The described invention provides a mobile cardiac monitoring device for monitoring a patient's heart rate and cardiac rhythm, acquired electrocardiogram (ECG) leads, and a cardiac electrical biomarker. The mobile cardiac monitoring device can derive a 12-lead ECG to at least 22 lead ECG (n-lead ECG) from three measured leads, and can calculate a dynamic cardiac electrical biomarker from the derived 12-lead ECG. The mobile cardiac monitoring device can communicate over a data network, such as a cellular network, to transmit an alert when a trigger condition is detected based on the dynamic cardiac electrical biomarker.

In one embodiment of the described invention, voltage-time measurements for a subset of ECG leads of a user are received at a mobile cardiac monitoring device. A full set of n-ECG leads for the user is derived from the subset of ECG leads. A heart rate of the user is calculated and a cardiac rhythm of the user is monitored based on at least one of the measured subset of ECG leads. A cardiac electrical biomarker (CEB) is calculated from the derived full set of ECG leads.

In another embodiment of the described invention, a mobile cardiac monitoring device comprises electrocardiogram (ECG) electrodes for acquiring voltage-time measurements for a subset of ECG leads of a user, an ECG derivation module for deriving a full set of ECG leads for the user from the subset of ECG leads, a heart rate calculation and cardiac rhythm monitoring module for calculating a heart rate and monitoring cardiac rhythm of the user based on at least one of the measured subset of ECG leads, and a cardiac electrical biomarker (CEB) calculation module for calculating a CEB from the derived full set of ECG leads.

In another embodiment of the described invention, a mobile cardiac monitoring device comprises a processor and a memory storing computer program instructions, which, when executed by the processor, cause the processor to perform operations comprising deriving a full set of electrocardiogram (ECG) leads for the user from a subset of ECG leads received from ECG electrodes, calculating a heart rate and monitoring a cardiac rhythm of the user based on at least one of the measured subset of ECG leads, and calculating a cardiac electrical biomarker (CEB) from the derived full set of ECG leads.

In another embodiment of the described invention, a system for cardiac monitoring of a plurality of patients comprises a plurality of cardiac monitoring devices and a central monitoring system. Each of the plurality of cardiac monitoring devices acquires voltage-time measurements for a subset of electrocardiogram (ECG) leads of a respective one of a plurality of patients. Each of the plurality of cardiac monitoring devices transmits the voltage-time measurements for the subset of ECG leads of the respective one of a plurality of patients via a network. The central monitoring system receives the voltage-time measurements for the subset of ECG leads for each of the plurality of patients transmitted from the plurality of cardiac monitoring devices. The central monitoring system derives a respective full set of ECG leads for each of the plurality of patients from the respective subset of ECG leads. The central monitoring system calculates a respective cardiac electrical biomarker (CEB) for each of the plurality of patients from the respective derived full set of ECG leads and detects whether a trigger condition occurs for each of the plurality of patients based on the respective CEB calculated for each of the plurality of patients.

These and other advantages of the invention will be apparent to those of ordinary skill in the art by reference to the following detailed description and the accompanying drawings.

DETAILED DESCRIPTION

The described invention relates to a mobile cardiac monitoring device. Embodiments of the described invention provide a mobile cardiac monitoring device for monitoring a patient's heart rate and cardiac rhythm, acquired electrocardiogram (ECG) leads, and a cardiac electrical biomarker. The mobile cardiac monitoring device can be used to monitor patients remotely and to monitor the development of cardiac diseases in real time.

Figure 1:
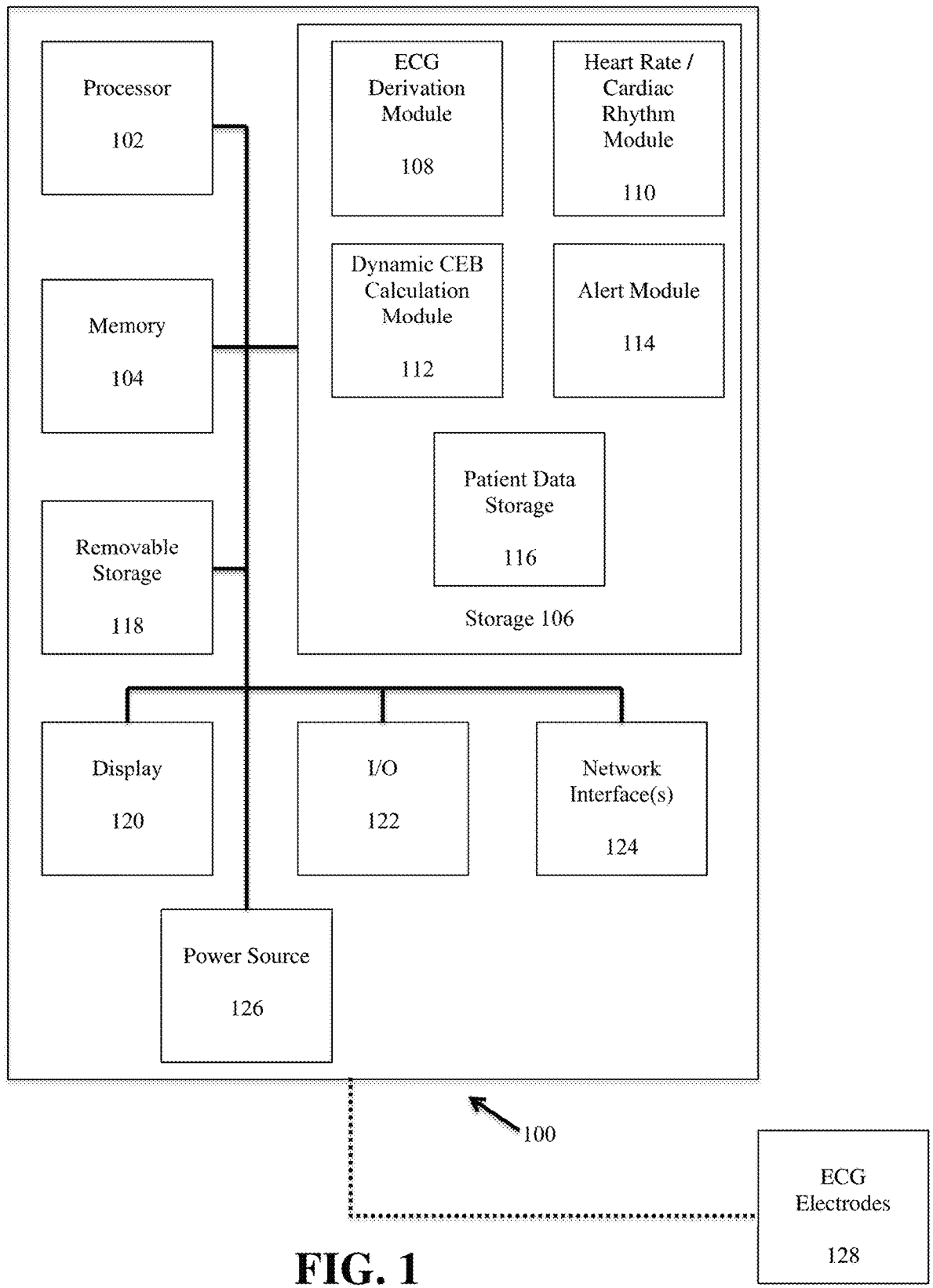
FIG. 1 illustrates a mobile cardiac monitoring device 100 according to an embodiment of the described invention.

FIG. 1 illustrates a mobile cardiac monitoring device 100 according to an embodiment of the described invention. The mobile cardiac monitoring device 100 can be implemented as a stand-alone device or can be implemented as part of another mobile device, such as a cellular phone, tablet, etc. According to an advantageous embodiment, the cardiac monitoring device 100 is a portable, hand-held device, and thus can be considered a "mobile" or "ambulatory" device. As illustrated in FIG. 1, the mobile cardiac monitoring device 100 includes a processor 102 operatively coupled to a data storage device 106 and a memory 104. The processor 102 controls the overall operation of cardiac monitoring device 100 by executing computer program instructions that define such operations. The computer program instructions may be stored in the data storage device 106, or the removable storage 118, and loaded into memory 104 when execution of the computer program instructions is desired. The electrocardiogram (ECG) derivation module 108, heart rate and cardiac rhythm module 110, dynamic cardiac electrical biomarker (CEB) module 112, and the alert module 114, as well as the method steps of FIGS. 3, 4, and 6, described below, can be defined by computer program instructions stored in the data storage device 106 and controlled by processor 104 executing the computer program instructions when the computer program instructions are loaded into the memory 104. For example, the computer program instructions can be implemented as computer executable code programmed by one skilled in the art to perform the method steps of FIGS. 3, 4, and 6 and the implement the modules 108, 110, 112, and 114 shown in FIG. 1.

The processor 102 may include both general and special purpose microprocessors, and may be the sole processor or one of multiple processors of the cardiac monitoring device 100. The processor 102 may include one or more central processing units (CPUs), for example. The processor may also include one or more graphics processing units (GPUs). The processor 102, data storage device 106, and/or memory 104 may include, be supplemented by, or incorporated in, one or more application-specific integrated circuits (ASICs) and/or one or more field programmable gate arrays (FPGAs).

The data storage device 106 and memory 104 each include a tangible non-transitory computer readable storage medium. The memory 104 may include high-speed random access memory, such as dynamic random access memory (DRAM), static random access memory (SRAM), double data rate synchronous dynamic random access memory (DDR RAM), or other random access solid state memory devices. The data storage device 106 may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices. The cardiac monitoring device 100 also includes removable storage 118. The removable storage 118 includes a port and corresponding removable storage medium. For example, the removable storage 118 can be a Secure Digital (SD) port and corresponding SD card, but the described invention is not limited thereto, and any other type of removable storage can be used as well.

The cardiac monitoring device 100 may also include a display 120, and one or more other input/output devices 122 that enable user interaction with the cardiac monitoring device 100. For example, the display 120 may be a liquid crystal display (LCD) displaying information to the user. The other input/output devices 122 can include input devices such as a touchscreen, keypad, buttons, etc., by which a user can provide input to cardiac monitoring device 100, input ports, such as a USB port, mini-USB port, micro-USB port, etc., and output devices such as speakers, a headphone jack, light emitting diodes (LEDs), etc. The cardiac monitoring device 100 also includes a power source 126, such as a rechargeable battery.

The cardiac monitoring device 100 may also include one or more network interfaces 124 for communicating with other devices via one or more networks. According to an advantageous embodiment, the network interfaces 124 can include a cellular network interface for communicating over a cellular network, such as Global System for Mobile Communications (GSM) network, Code Division Multiple Access (CDMA) network, or Long Term Evolution (LTE) network. Such a cellular network may be a 3G or 4G network, over which data can be transmitted. The network interfaces 124 can also include a short message service (SMS) and/or multi-media message service (MMS) network interface for transmitting and receiving text messages and/or multi-media messages. The network interfaces 124 may also include a wireless network interface controller (WNIC) for wireless communications over a data network, such as a WIFI network. The network interfaces 124 may also include a network interface for short range wireless networks, such as Bluetooth.

The mobile cardiac monitoring device 100 is communicatively coupled to ECG electrodes 128. In one embodiment, the ECG electrodes can be connected to the cardiac monitoring device 100 via a cable. For example, the ECG electrodes 128 can be connected to a USB cable that is inserted into a USB port of the mobile. It is to be understood that the described invention is not limited to a USB cable and other types of cables may be used as well. In another embodiment, the ECG electrodes 128 may communicate with the mobile cardiac monitoring device 100 wirelessly. For example, the ECG electrodes 128 may communicate with the mobile cardiac monitoring device 100 via a Bluetooth connection. The ECG electrodes 128 are placed on the body of a user or patient and transmit voltage-time measurements for a subset of ECG leads to the mobile cardiac monitoring device 100. According to an advantageous embodiment, voltage-time measurements for three ECG leads are received from the ECG electrodes 128. In an exemplary implementation, ECG leads I, II, and V2 are measured by the ECG electrodes 128. In another possible implementation, ECG leads I, aVF, and V2 can be measured by the ECG electrodes 128. The ECG electrodes 128 can include five electrodes to measure the three ECG leads, where one of the electrodes is a ground. In a possible embodiment, the ground can be included in one of the other electrodes and fewer total electrodes can be used.

Figure 2:
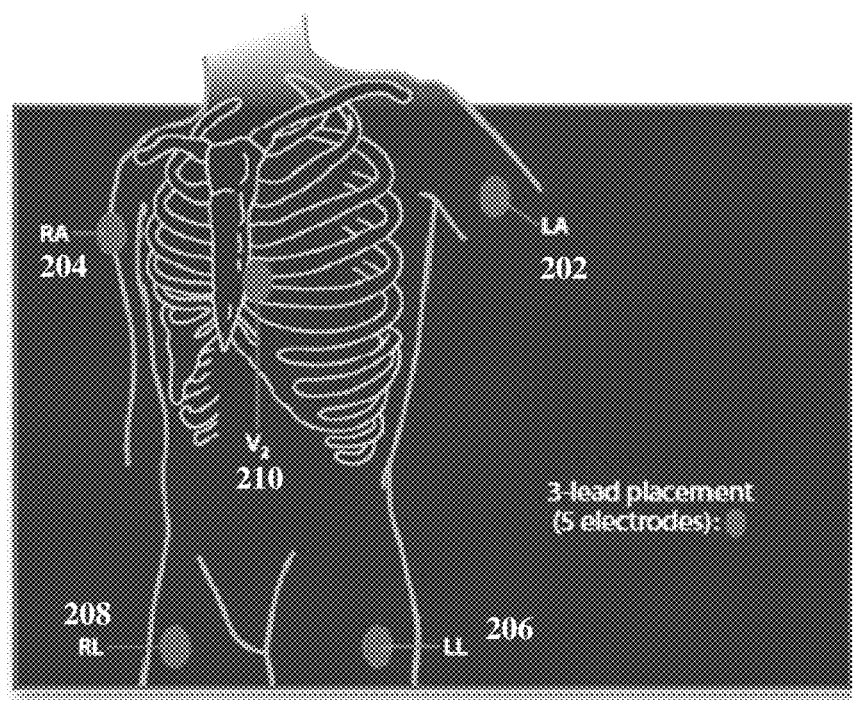
FIG. 2 illustrates placements of ECG electrodes on the body of a user according to an embodiment of the described invention.

FIG. 2 illustrates placements of the ECG electrodes on the body of a user according to an embodiment of the described invention. As shown in FIG. 2, five electrodes 202, 204, 206, 208, and 210 are placed on the user. Electrode 202 is placed on the left arm (LA), electrode 204 is placed on the right arm (RA), electrode 206 is placed on the left leg (LL), electrode 208 may be placed on the right leg (RL), and electrode 210 is placed at the V2 lead location, which is at the fourth interspace near the sternum. Electrodes 202, 204, and 206 can be placed anywhere on their corresponding limbs, making their placement easy for a user. Electrode 208 is a ground and is typically placed on the right leg, making its placement easy for a user, but the location of the ground electrode is not limited to the right leg and can be placed in other locations as well. Electrode 210 also corresponds to an anatomical location that is easy for a user to locate. The signal from the electrodes may be improved if the electrodes are not placed directly on a muscle, which can cause interference. In an exemplary alternative implementation, a ground can be included in the V2 electrode (210). In this case, electrode 208 is not needed and four electrodes can be used instead. In other possible implementations, the ground can be in one of the other electrodes as well. Using the electrode placements of FIG. 2, the ECG electrodes measure ECG leads I, II, and V2, which are members of the set of leads that makes up the standard 12-lead ECG. Those who are knowledgeable in the art will recognize that other electrodes placed on the body surface to record other basis orthogonal lead sets may be utilized as well. For example, placement of V9 in the posterior chest (behind V2) can be in place of V2 in the above described example to derive the n-lead ECG and construct the CEB.

Returning to FIG. 1, the ECG derivation module 108, heart rate and cardiac rhythm module 110, dynamic CEB calculation module 112, and alert module 114 can be stored in the data storage device 106. Each of these modules includes computer program instructions for performing a particular set of operations when loaded into the memory 104 and executed by the processor 102. The data storage device 106 also includes patient data storage 116 for storing various patient data, including voltage-time measurements received from the ECG electrodes 128, derived ECG data generated by the ECG derivation module 108, heart rate and cardiac rhythm data generated by the heart rate and cardiac rhythm module 110, and cardiac electrical biomarker (CEB) data generated by the dynamic CEB calculation module 112.

A standard ECG is measured by placing a series of electrodes on the patient's skin. The standard ECG record includes 12 lead waveforms, denoted as I, II, III, aVR, aVL, aVF, V1, V2, V3, V4, V5, and V6, arranged in a specific order that is interpreted by a physician using pattern recognition techniques. In the usual configuration, 10 electrodes are placed on the body torso to measure the electrical potentials that define the standard 12 leads. According to an embodiment of the described invention, the ECG derivation module 108 can derive a full set of ECG leads from the subset of ECG leads measured by the ECG electrodes 128.

According to some such embodiments of the described invention, the ECG derivation module 108 can derive a complete n-lead (e.g., 12-lead) ECG for a patient from the 3 measured leads received from the ECG electrodes 128. The ECG derivation module 108 can derive the complete n-lead ECG from the 3 measured leads by applying a stored universal transformation matrix that is generated from sets of training ECG data using abstract factor analysis and a simplex optimization algorithm. Such a method for deriving an n-lead ECG is described in greater detail in U.S. Pat. No. 6,901,285, which is incorporated herein by reference in its entirety.

Figure 3:
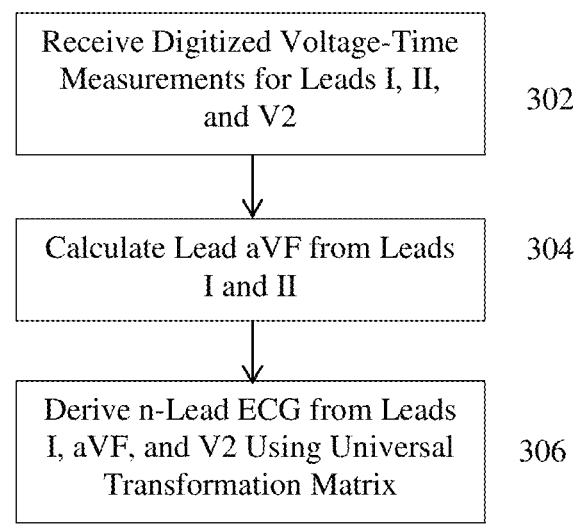
FIG. 3 illustrates a method for deriving an n-lead ECG according to an embodiment of the described invention.

FIG. 3 illustrates a method for deriving an n-lead ECG according to an embodiment of the described invention. The method steps of FIG. 3 can be performed by the ECG derivation module 108 to derive a complete n-lead ECG from the voltage-time measurements for 3 ECG leads received from the ECG electrodes 128. Referring to FIG. 3, at step 302, digitized voltage-time measurements for ECG leads I, II, and V2 are received from the ECG electrodes 128. Lead I is the voltage between the left arm (LA) electrode and right arm (RA) electrode: Lead I=LA−RA. Lead II is the voltage between the left leg (LL) electrode and the RA electrode: Lead II=LL−RA. Lead V2 is the voltage between the positive pole at the V2 electrode and a negative pole that is a composite pole known as Wilson's central terminal, which is produced by averaging the measurements from the electrodes RA, LA, and LL to give an average potential across the body: Lead V2=V2−⅓(RA+LA+LL).

At step 304, the aVF ECG lead is calculated from the measured ECG leads I and II. The aVF (augmented vector foot) lead can be calculated from the known geometry of leads I and II. The aVF lead has a positive pole on the left leg and the negative pole is a combination of the right arm electrode and the left arm electrode. Due to the built in redundancy in the standard 12-lead ECG, the measurement of any 2 of the first 6 leads can be used to calculate the other 4 leads according to the following geometrically based formulae:

Lead III=Lead II−Lead I

Lead aVR=−0.87×((Lead I+Lead II)/2)

Lead aVL=0.87×((Lead I−Lead III)/2)

Lead aVF=0.87×((Lead II+Lead III)/2).

Accordingly, the aVF lead can be calculated from the lead I and lead II as: Lead aVF=[((2×Lead II)−Lead I)/2]×0.87. This results in three orthogonal leads of I, aVF, and V2. According to an alternate embodiment, the above equations can also be calculated without the 0.87 coefficients, such that the following equations are used for Lead aVR, Lead aVL, and Lead aVF: Lead aVR=−((Lead I+Lead II)/2); Lead aVL=((Lead I−Lead III)/2); and Lead aVF=((Lead II+Lead III)/2). Although the method of FIG. 3 acquires the voltage-time measurements for leads I, II, and V2, and then calculates lead aVF from leads I and II, in an alternative embodiment, voltage time measurements for leads I, aVF, and V2 can be acquired directly from the ECG electrodes. For example, lead aVF can be acquired as: Lead aVF= LL−½(RA+LA).

At step 306, an n-lead ECG is derived from leads I, aVF, and V2 using a universal transformation matrix. The universal transformation matrix is derived from training sets of ECG data and stored as part of the ECG derivation module 108 in the data storage device 106. Without limitation, examples of lead sets that can be derived from the 3 leads (I, aVF, and V2) are:

12 leads: I, II, III, aVR, aVL, aVF, V1, V2, V3, V4, V5, V6;

15 leads: I, II, III, aVR, aVL, aVF, V1, V2, V3, V4, V5, V6, X, Y, Z;

15 leads: I, II, III, aVR, aVL, aVF, V1, V2, V3, V4, V5, V6, V7, V8, V9;

16 leads: I, II, III, aVR, aVL, aVF, V1, V2, V3, V4, V5, V6, V3R, V4R, V5R, V6R;

18 leads: I, II, III, aVR, aVL, aVF, V1, V2, V3, V4, V5, V6, V7, V8, V9, X, Y, Z;

22 leads: I, II, III, aVR, aVL, aVF, V1, V2, V3, V4, V5, V6, V7, V8, V9, V3R, V4R, V5R, V6R, X, Y, Z.

The universal transformation matrix is particular to the number of leads in the n-lead ECG being derived. The universal transformation matrix is generated from a training set of ECG voltage-time data arrays. In particular, an abstract factor analysis ("AFA") technique can be applied to each ECG voltage-time array in the training set in order to minimize the error in the measured arrays. A simplex optimization technique ("SOP") is then applied to the training set in order to derive the universal transformation matrix that is applicable to all patients and is time independent. In addition to being time independent, the universal transformation matric can also be independent to other characteristics such as gender, body type, etc. However, it is also possible that more specific transformation matrixes can be utilized for specific characteristics such as gender, body type, gender, etc., based on the training data used to derive the universal transformation matrix. The universal transformation matrix is an N×3 matrix that is applied to the subset of 3 leads to generate the full n-lead ECG. In particular, the N×3 universal transformation matrix is multiplied by a vector comprising 3 leads {I, aVF, V2} for a particular time to yield a full n-lead ECG. It with be understood by those knowledgeable in the art that {I, aVF, V2} proximates a basis orthogonal lead set that is necessary to construct the universal transformation matrix. Other such basis orthogonal lead sets may be used to perform this step, as will be recognized by those knowledgeable in the art. For example, other exemplary basis orthogonal lead sets include {I, aVF, V9}, {V6R, aVF, V2}, and {V6R, aVF, V9}, but the present invention is not limited thereto.

Returning to FIG. 1, the heart rate and cardiac rhythm module 110 identifies the cardiac rhythm and calculates a heart rate of the user from at least one of the measured ECG leads. ECG is typically presented as a graph plotting electrical activity of the heart on the vertical axis against time on the horizontal axis. Standard ECG paper moves at 25 mm per second during real-time recording. This means that when looking at a printed ECG a distance of 25 mm along the horizontal axis represents 1 second. ECG paper is marked with a grid of small and large squares. Each small square represents 40 milliseconds (ms) in time along the horizontal axis and each larger square contains 5 small squares, thus representing 200 ms. Standard paper speeds and square markings allow easy measurement of cardiac timing intervals. This enables calculation of heart rates and identification of abnormal electrical conduction within the heart. On the ECG, the amplitude or voltage of the recorded electrical signal is expressed in the vertical dimension and is measured in millivolts (mV). On standard ECG paper, 1 mV is represented by a deflection of 10 mm.

Figure 4:
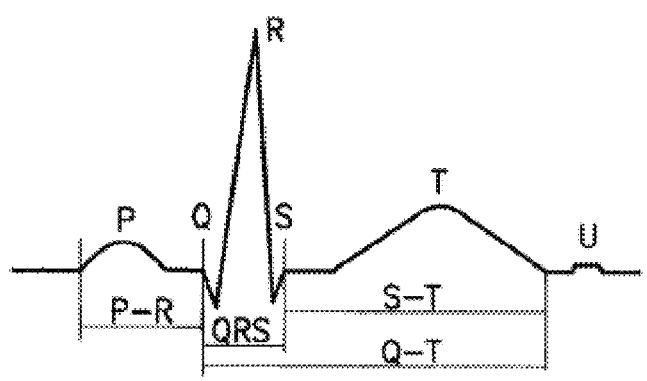
FIG. 4 illustrates a typical cardiac electrical signal as measured by an ECG.

FIG. 4 illustrates a typical cardiac electrical signal as measured by an ECG. Since the first structure to be depolarized during normal sinus rhythm is the right atrium, closely followed by the left atrium, the first electrical signal on a normal ECG originates from the atria and is known as the P wave. Although there is usually only one P wave in most leads of an ECG, the P wave is in fact the sum of the electrical signals from the two atria, which are usually superimposed. There is a short, physiological delay as the atrioventricular (AV) node slows the electrical depolarization before it proceeds to the ventricles that is responsible for the PR interval, a short period where no electrical activity is seen on the ECG, represented by a straight horizontal or "isoelectric" line. Depolarization of the ventricles results in the QRS complex, which is usually the largest portion of the ECG signal. The Q wave is the first initial downward or negative deflection is the first initial downward of negative deflection, the R wave is the next upward deflection, and the S wave is the next deflection downwards. An electrical signal reflecting repolarization of the myocardium I shown as the ST segment and the T wave. The ST segment is normally isoelectric, and the T wave in most leads in an upright deflection of variable amplitude and duration. The T wave may be followed by an additional low-amplitude wave known as the U wave. This late repolarization normally has the same polarity as the preceding T wave. A PR interval is measured from the beginning of the P wave to the first deflection of the QRS complex and has a normal range of 120-200 ms (3-5 small squares on ECG paper). The QRS duration is measured from the first deflection of the QRS complex to the end of the QRS complex at the isoelectric line and has a normal range of up to 120 ms (3 small squares on ECG paper). The QT interval is measured from the first deflection of the QRS complex to the end of the T wave at the isoelectric line and has a normal range of up to 440 ms, although this varies with heart rate and may be slightly longer in females.

The heart rate and cardiac rhythm module 110 can calculate the heart rate of the patient by determining an amount of time between each QRS complex in one or multiple ECG leads. Each second of time in the ECG signal can be estimated by 25 mm (5 large squares) along the horizontal axis. Accordingly, the number of large squares between each QRS complex of the ECG lead provides an approximate amount of time between each QRS complex, which can be used to estimate the heart rate. For example, if the number of large squares between each QRS complex is 5, the heart rate is 60 beats per minute; if the number of large squares between each QRS complex is 3, the heart rate is 100 beats per minute; if the number of large squares between each QRS complex is 2, the heart rate is 150 beats per minute. It is to be understood that the standard paper rate and square markings can be scaled for display of the ECG signals on the display 120, and the heart rate can be similarly estimated. The heart rate and cardiac rhythm module 110 can also evaluate the acquired and/or derived ECG signals to monitor the cardiac rhythm to help identify whether the cardiac rhythm is regular or irregular.

The dynamic CEB calculation module 112 calculates a CEB from the derived ECG. The CEB is an electrical biomarker that quantifies dipolar energy content in the cardiac electrical field. The more dipolar energy content that is present in the cardiac electrical field, the more normal is the patient's condition, while the more multipolar energy content that is present in the cardiac electrical field, the more abnormal is the patients' condition. The CEB can be used as a "point-of-care" diagnostic test to detect the presence or absence of acute myocardial ischemic injury (AMII) including acute myocardial infarction (AMI). The CEB can also be used to monitor a patient who is not initially diagnosed with AMII/AMI to monitor and detect the onset and/or development of AMII/AMI in real time. The electrical field of the heart starts at a cellular level and there is a very small multi-polar component to the electrical field in cases of AMII/AMI. The CEB measures dipolar electrical activity in the electrical field of the heart.

According to an embodiment of the described invention, the CEB can be calculated from the derived ECG by calculating the third eigenvalue of the derived ECG voltage-time data. In particular, abstract factor analysis (AFA) can be used to calculate eigenvectors of the derived ECG voltage-time data. Let D represent the data matrix array of the derived ECG voltage-time data. A covariance matrix Z can then be constructed by multiplying D by its transpose matrix as follows: $Z=D^T D$. The covariance matrix Z is then diagonalized by finding a matrix Q such that $Q^{-1}ZQ=[\lambda_j \delta_{jk}]$, where $d_{jk}$ is the Kronecker delta such that $d_{jk}=0$ if $j \neq k$ and $d_{jk}=1$ if $j=k$, and $\lambda_j$ is an eigenvalue of the set of equations $Zq_j=\lambda_j q_j$, where $q_j$ is the j-th column of Q eigenvectors. The third eigenvalue ($\lambda_3$) as calculated is used as the CEB. The present inventor has determined that the third eigenvalue, which provides a measurement of dipolar activity of the cardiac electrical field, can be used as a CEB that is indicative of acute myocardial ischemic injury. In general, the more multipolar (less dipole) forces in the cardiac electrical field, the greater the potential for an AMII/AMI. The CEB has a numerical value that quantifies the multipolar forces in the cardiac electrical field suggestive of an AMI. For example, a CEB value less than 66 can be indicative of a normal condition, a CEB value between 66 and 94 can be considered to be in an indeterminate zone, and a CEB value greater than 94 can be indicative of an abnormal condition. It is to be understood that the present invention is not limited to these particular cutoff values, and the cutoff values may vary based on user operability and variation of a more specific universal transformation matrix.

In an advantageous embodiment of the described invention, the dynamic CEB calculation module 112 calculates a dynamic CEB by calculating a respective CEB value from the derived ECG for each heartbeat. In this case, the abstract factor analysis is applied to the derived ECG voltage-time data for each heartbeat to calculate the third eigenvalue of the derived ECG voltage-time data for each heart, resulting in a respective CEB value for each heartbeat. The dynamic CEB data can be displayed by the display 120 as a graph of CEB over time. In another possible embodiment, a number of heart beats in the derived ECG in a predetermined time interval (e.g., 10 seconds) are averaged into a median beat, and a static CEB is calculated for that time interval based on the median beat ECG data. In generating a median beat, beats of the same shape are combined into an accurate representative cycle. Noise is dramatically reduced by this process. Successive CEB's in a predetermined interval of time can lead to the display of a dynamic CEB in this instance.

In another possible embodiment, a fractal CEB may be calculated instead of or in addition to the eigenvalue CEB. The fractal CEB can be calculated using the method described in U.S. Pat. No. 6,920,349, which is incorporated by reference herein in its entirety. In this case, a spatial curve can be defined from the lead values for at least three leads of the derived ECG. A fractal index for the spatial curve is calculated as a function of time. As an example, the time rate of change of the fractal index can be calculated as the CEB. A negative time rate of change is indicative of normal cardiac activity, while a positive time rate of change is indicative of pathological activity. In a possible implementation, the dynamic CEB calculation module 112 may calculate both the eigenvalue CEB and the fractal CEB for each heart beat and the alert module 114 may utilize a combination of the eigenvalue CEB and the fractal CEB in determining whether an alert condition has been triggered. Other fractal analyses of the spatial curves can be constructed as well. A suite of multiple CEBs can be calculated and displayed and/or transmitted to a device associated with a physician to assist the physician in understanding the onset and/or development of AMII/AMI.

The alert module 114 monitors the CEB values calculated by the dynamic CEB calculation module 112 and controls the mobile cardiac monitoring device 100 to send an alert when a certain trigger condition is detected. In a possible embodiment, the alert module 114 may monitor dynamic CEB values calculated for each heart beat and determine whether the CEB value for each heart beat is in an abnormal zone. For example, for the eigenvalue CEB, a CEB value greater than 94 can be considered to be in the abnormal zone. If a programmable percentage of the heart beats in the abnormal zone within a predetermined time interval is greater than a threshold, the alert module 114 determines that the trigger condition has been detected and transmits an alert message via the network interface(s) 124. For example, the alert message can be a text message sent to a predetermined remote device, such as device associated with a physician of the patient. The text message can include the derived ECG data and/or the measured ECG leads, the estimated heart rate data, and the CEB data for a certain time period preceding the detection of the trigger condition. Similarly, the alert message may be an email message sent to a predetermined email address, and the email message may include the derived ECG data and/or the measured ECG leads, the heart rate data, and the CEB data of the patient. The alert module 114 may also control the mobile cardiac monitoring device 100 to place a telephone call to a telephone number associated with a predetermined remote device (e.g. the telephone of the physician), and play a predetermined voice alert message. The alert module 114 may also control the mobile cardiac monitoring device 100 to automatically contact and emergency response system. For example, the alert module may control the mobile cardiac monitoring device 100 to automatically call 911 in response to the detection of a trigger condition. In a possible embodiment, the data can be downloaded to a reader device, such as a Vetraplex ECG System, that is capable of performing additional calculations and displaying additional information. For example, such a device may derive a 15 or 22 lead ECG from the measured ECG leads, display the derived 15 or 22 lead ECG.

Figure 5:
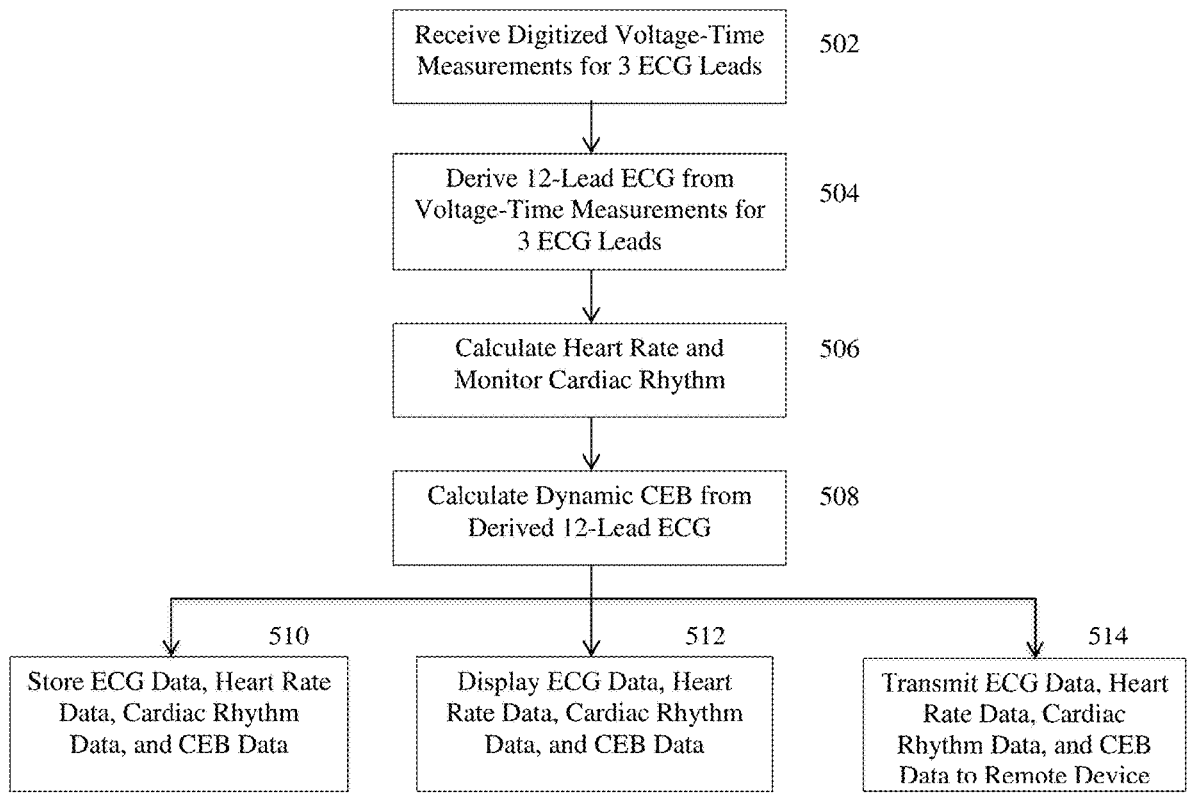
FIG. 5 illustrates a method of cardiac monitoring using a mobile cardiac monitoring device according to an embodiment of the described invention.

FIG. 5 illustrates a method of cardiac monitoring using a mobile cardiac monitoring device according to an embodiment of the described invention. The method of FIG. 5 may be performed by the mobile cardiac monitoring device 100 of FIG. 1. The method steps of FIG. 5 can be repeated to provide real-time cardiac monitoring for a patient. In an exemplary implementation, a mobile cardiac monitoring device 100 can be provided to a patient who is not under direct supervision of a doctor, such as a patient who exhibited chest pain but was sent home from an emergency room, and the method of FIG. 5 can be performed to provide real-time remote cardiac monitoring of the patient. In another exemplary implementation, the method of FIG. 5 can be performed for real-time point of care of a patient in a hospital, doctor's office, etc.

Referring to FIG. 5, at step 502, digitized voltage-time measurements are received for 3 ECG leads. For example, voltage time measurements for leads I, II, and V2 or for leads I, aVF, and V2 can be received from the ECG electrodes 128. At step 504, a full 12-lead ECG is derived from the voltage-time measurements for the 3 ECG leads. As described above, the ECG derivation module can derive the 12-lead ECG using a pre-stored universal transformation matrix. Although the method of FIG. 5 derives a 12-lead ECG, the described invention is not limited thereto, and any other n-lead ECG can be similarly derived. For example, the mobile cardiac monitoring device may derive a full 15-lead or 22-lead ECG. At step 506, the heart rate of the patient is calculated from the received voltage time measurements for at least one of the ECG leads and the cardiac rhythm is monitored. At step 508, a dynamic CEB is calculated from the derived 12-lead ECG. The dynamic CEB can be constructed by calculating a CEB value for each heartbeat. The CEB value for each heart beat can be constructed by calculating the third eigenvalue of the derived 12-lead ECG voltage-time data corresponding to each heartbeat. It is also possible that other eigenvalue analyses can be performed as well.

The method of FIG. 5 then proceeds to three possible steps (510, 512, and 514). According to various embodiments, the mobile cardiac monitoring device 100 may perform any one of these steps, all of these steps, or any combination of these steps. At step 510, the derived ECG data, the heart rate data, the cardiac rhythm data, and the CEB data for the patient are stored. This patient data can be stored in the patient data storage 116 of the data storage device 106 and/or on the removable storage device 118. In a possible implementation, the mobile cardiac monitoring device 100 can be used to monitor a patient for a specific time period (e.g., 1 or 2 days) and the patient data acquired during that time period is stored on the removable storage device 118. A doctor can then remove the removable storage 118 and load the patient data from the removable storage to the doctor's computer (or other device) in order to view the patient data.

At step 512, the derived ECG data, the heart rate data, the cardiac rhythm data, and the CEB data of the patient may be displayed on the display 120 of the mobile cardiac monitoring device 100. The patient data can be displayed in real-time as the patient data is acquired and calculated. The derived ECG data can be displayed by displaying the ECG signals over time for each of the leads of the derived 12-lead ECG. It is also possible that the ECG data can be displayed by displaying a 3-dimensional spatial ECG loop resulting from plotting the 3 measured leads (I, aVF, and V2) or any other 3 orthogonal leads of the derived 12-lead ECG against each other in 3-dimensional space. It is also possible that the mobile cardiac monitoring device can display the ECG vector loops from a full 15-lead and/or 22-lead ECG derived by the mobile cardiac monitoring device. The heart rate can be displayed as a numeric value that is updated as needed. Dynamic CEB data, such as CEB values calculated for each heartbeat or for predetermined intervals of heartbeats, can be displayed as a graph of CEB over time. The Dynamic CEB data can be displayed in real-time as it is calculated. It is also possible to display dynamic or static CEB data as a numeric value that is updated as it changes. In a possible embodiment, the CEB data can be color coded, for example using different colors for CEB values corresponding to a normal zone, an indeterminate zone, and an abnormal zone.

At step 514, the derived ECG data, the heart rate data, the cardiac rhythm data, and the CEB data of the patient is transmitted to a remote device. For example, the patient data can be transmitted to a computer or other device associated with a doctor or a remote monitoring system. For example, the data can be transmitted to a reader device, which can calculate a 15 or 22 lead ECG of the patient. In another possible embodiment, the full 15 and/or 22 lead ECG can be derived by the cardiac monitoring device and transferred to the remote device. The patient data can be transmitted in real-time as it is acquired and calculated. This allows a doctor to monitor the patient data in real-time even if the patient is located remotely. In another possible implementation, the patient data can be transmitted at programmable time intervals. In another possible implementation, the patient can manually trigger the mobile cardiac monitoring device 100 to transmit the data. For example, the mobile cardiac monitoring device may be equipped with an event button that the patient/user can select to manually trigger the patient data to be transmitted. The patient data may be transmitted via any type of data network, such as a cellular network, WIFI, text or multimedia messaging, Bluetooth, etc., using the network interface(s) 124. In a possible implementation, the patient data can be transmitted to a monitoring service, which can then monitor the patient data to detect emergency conditions instead of or in addition to an alert module 114 in the mobile cardiac monitoring device 100.

Figure 6:
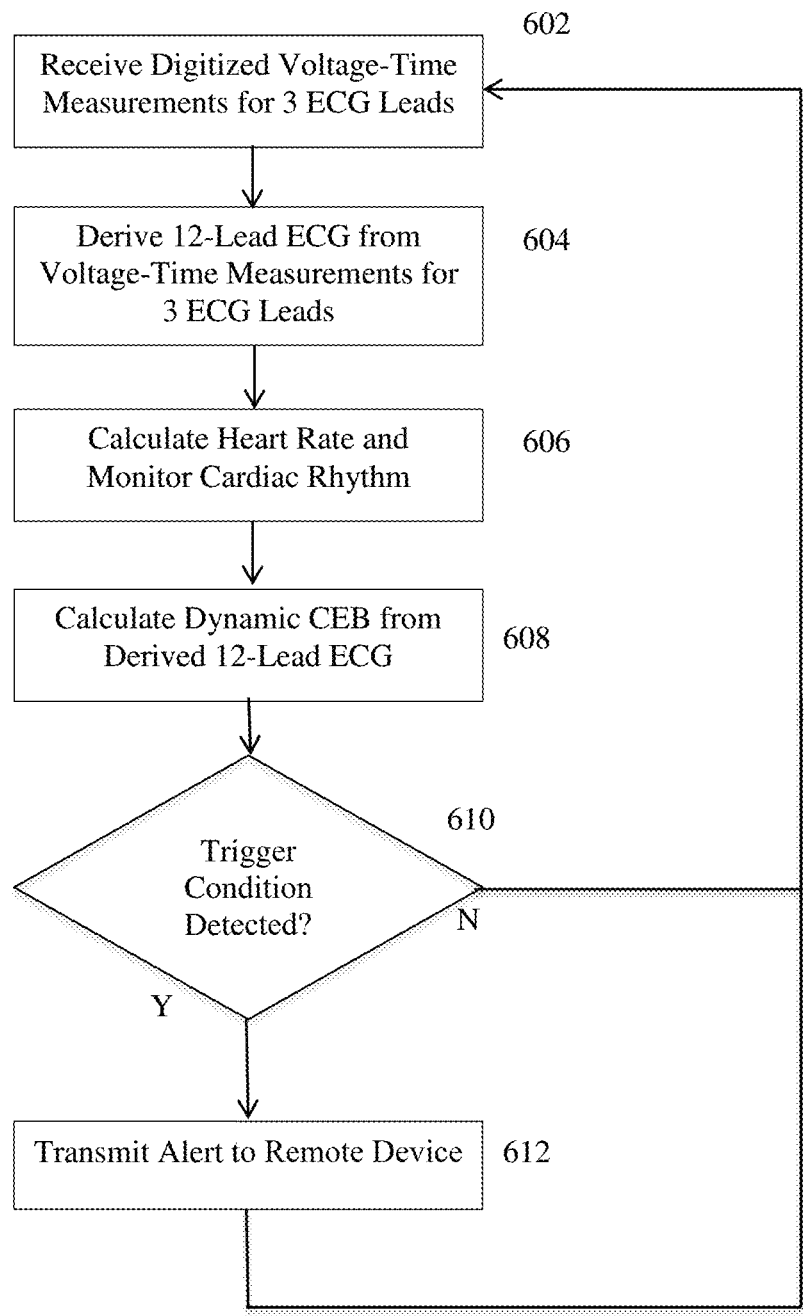
FIG. 6 illustrates a method of cardiac monitoring and alert notification using a mobile cardiac monitoring device according to an embodiment of the described invention.

FIG. 6 illustrates a method of cardiac monitoring and alert notification using a mobile cardiac monitoring device according to an embodiment of the described invention. The method of FIG. 6 may be performed by the mobile cardiac monitoring device 100 of FIG. 1. The method steps of FIG. 6 can be repeated to provide real-time cardiac monitoring for a patient. In an exemplary implementation, a mobile cardiac monitoring device 100 can be provided to a patient who is not under direct supervision of a doctor, such as a patient who exhibited chest pain but was sent home from an emergency room, and the method of FIG. 6 can be performed to provide real-time cardiac monitoring of the patient. In another exemplary implementation, the method of FIG. 6 can be performed for real-time point of care of a patient in a hospital, doctor's office, etc.

Referring to FIG. 6, at step 602, digitized voltage-time measurements are received for 3 orthogonal ECG leads. For example, voltage time measurements for leads I, II, and V2 or for leads I, aVF, and V2 can be received from the ECG electrodes 128. At step 604, a full 12-lead ECG is derived from the voltage-time measurements for the 3 ECG leads. As described above, the ECG derivation module can derive the 12-lead ECG using a pre-stored universal transformation matrix. Although the method of FIG. 5 derives a 12-lead ECG, the described invention is not limited thereto, and any other n-lead ECG can be similarly derived. At step 606, the heart rate of the patient is calculated from the received voltage-time measurements for at least one of the ECG leads and the cardiac rhythm is monitored. At step 608, a dynamic CEB is calculated from the derived 12-lead ECG. The dynamic CEB can be constructed by calculating a CEB value for each heartbeat or for a particular interval of heartbeats. The CEB value for each heart beat can be constructed by calculating the eigenvalues of the derived 12-lead ECG voltage-time data corresponding to each heartbeat.

At step 610, it is determined if a trigger condition is detected. In order to determine if a trigger condition is detected, it is determined, for each heartbeat (or interval of heartbeats), whether a CEB associated with that heart beat is in an abnormal zone. For example, for eigenvalue CEB, a CEB value greater than 94 may be considered to be in an abnormal zone. A trigger condition can be detected when a programmable percentage of heart beats having a CEB value in the abnormal zone within a predetermined time interval is greater than a threshold. That is a trigger condition is detected when P>τ, where P is the percentage of heart beats in a time interval t (e.g., 1 minute) that have a CEB value in the abnormal zone, and τ is a threshold percentage value (e.g., 90%). It is also possible that the trigger condition can be detected based on an average CEB value over a certain time interval, based on a static eigenvalue CEB value calculated for a median heart beat for a certain time interval, based on a fractal CEB, or based on a combination of a fractal and an eigenvalue CEB or other combination of CEBs. If no trigger condition is detected, the method returns to step 602 and continues monitoring the patient by repeating steps 602, 604, 606, and 608. If a trigger condition is detected, the method proceeds to step 610.

At step 612, when a trigger condition is detected, an alert is transmitted to a predetermined remote device. The alert can be a text message sent to the predetermined remote device, such as advice associated with a doctor of the patient, via text message, email, telephone call, or any other type of message. The alert message, such as a text message or email, can include the derived ECG data, the calculated heart rate data, cardiac rhythm information, and the CEB data for a certain time period preceding the detection of the trigger condition. In addition to an alert message including the patient data, a telephonic alert message with a predetermined voice message can be placed to a predetermined telephone number. The method returns to step 602 and continues monitoring the patient by repeating steps 602, 604, 606, and 608.

Figure 7:
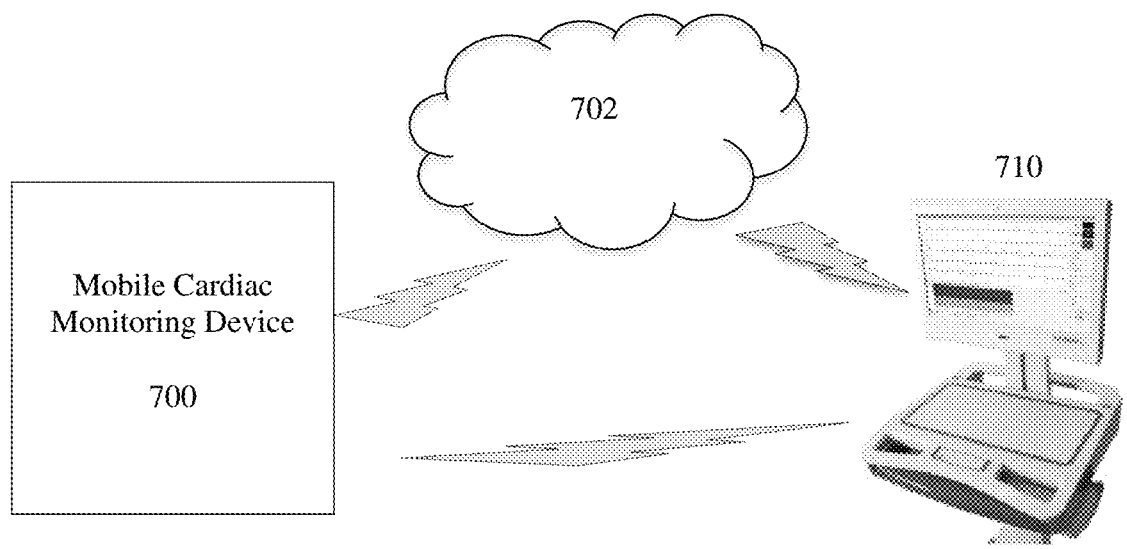
FIG. 7 illustrates communication between a mobile cardiac monitoring device 700 and a reader device 710 according to an embodiment of the present invention.

As described above, the mobile cardiac monitoring device may transmit data to a remote device. FIG. 7 illustrates communication between a mobile cardiac monitoring device 700 and a reader device 710 according to an embodiment of the present invention. The mobile cardiac monitoring device 700 can be implemented similarly to the mobile cardiac monitoring device 100 of FIG. 1. The reader device 710 is a device that can received data from the mobile cardiac monitoring device 700, derive additional information from the data, and display that information to a physician. For example, the reader device may be a VetraplexECG System located at a physician's office or hospital. According to a possible implementation, the mobile cardiac monitoring device 700 may send the acquired voltage-time measurements for the subset of ECG leads to the reader device 710. In other possible implementations, additional data such as calculated CEB values, heart rate data, cardiac rhythm data, and/or the derived 12 lead ECG data may also be sent from the mobile cardiac monitoring device 700 to the reader device 710. The mobile cardiac monitoring device 700 may send the data directly to the reader device 710 using any type of data transmission protocol. It is also possible that the mobile cardiac monitoring device may upload the data to a data network or "cloud" 702, which can then transmit the data to the reader device 710 and/or other remote devices associated physicians. The reader device 710 may derive a full 15 or 22 lead ECG for the patient based on the acquired subset of ECG leads or the derived 12 lead ECG data received from the mobile cardiac monitoring device 700, and display the derived 15 or 22 lead ECG for the physician. The reader device may also calculate a static CEB value based on the derived n-lead ECG and display the CEB value. In an exemplary implementation, the mobile cardiac monitoring device 700 can transmit the data to the reader device 710 (or to the cloud 702) at predetermined (programmable)

time intervals. It is also possible that the mobile cardiac monitoring device 700 can transmit the data to the reader device 710 (or to the cloud 702) in response to detection of an alert condition at the mobile cardiac monitoring device or in response to a manual trigger (e.g., selection of event button) input by the patient at the mobile cardiac monitoring device 700. It is also possible that the mobile cardiac monitoring device 700 can transmit the data to the reader device 710 (or to the cloud 702) in response to a request for data being received at the mobile cardiac monitoring device 700.

Figure 8:
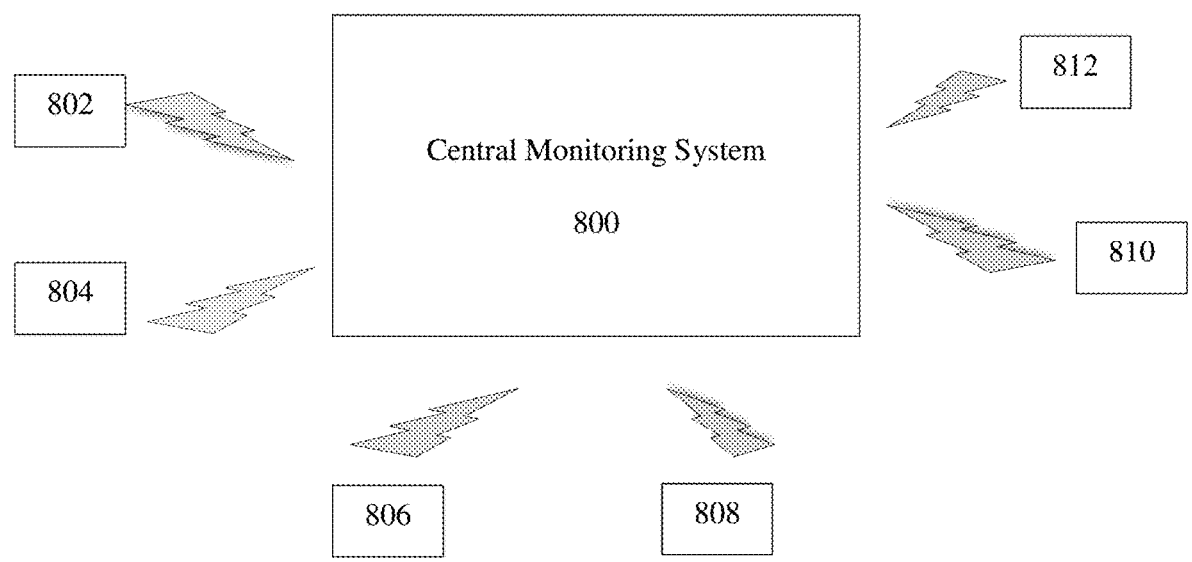
FIG. 8 illustrates a system for cardiac monitoring of a patient according to an embodiment of the described invention.

FIG. 8 illustrates a system for cardiac monitoring of a patient according to an embodiment of the present invention. As illustrated in FIG. 8, the system includes a central monitoring system 800 and a plurality of mobile cardiac monitoring devices 802, 804, 806, 808, 810, and 812. The mobile cardiac monitoring devices 802, 804, 806, 808, 810, and 812 can be implemented similarly to the mobile cardiac monitoring device 100 of FIG. 1. It is also possible that the mobile cardiac monitoring devices 802, 802, 806, 808, 810, and 812 of FIG. 8 can be implemented without the alert module 114, or without any of the ECG derivation module 108, the cardiac rhythm estimation module 110, the dynamic CEB calculation module 112, and the alert module 114. The mobile cardiac monitoring devices 802, 804, 806, 808, 810, and 812 are each associated with a respective patient and transmit respective patient data to the central monitoring system 800. The central monitoring system 800 monitors the patient data for each of the patients associated with the mobile cardiac monitoring devices 802, 804, 806, 808, 810, and 812. The mobile cardiac monitoring devices 802, 804, 806, 808, 810, and 812 can transmit the patient data via any type of data network, such as WIFI, Bluetooth, etc. In one example, the system of FIG. 8 can be implemented in a hospital and each patient can be provided with one of mobile cardiac monitoring devices 802, 804, 806, 808, 810, and 812. The central monitoring system 800 can then be used to simultaneously monitor all of the patients, or all patients on a floor or section of the hospital.

In one possible implementation, each of the mobile cardiac monitoring devices 802, 804, 806, 808, 810, and 812 acquires 3-lead ECG voltage-time measurements for the respective patient and transmits the 3-lead ECG voltage-time measurements to the central monitoring system 800. The central monitoring system then derives the full n-lead (e.g., 12-lead) ECG for each patient, estimates the heart rate for each patient based on the derived ECG, and dynamically calculates the CEB for each patient based on the derived ECG. In an exemplary implementation, central monitoring system 800 can derive a 15 or 22 lead ECG for each patient. The central monitoring system 800 also monitors the patient CEB data calculated for each patient to detect a trigger condition. In an advantageous implementation, the central monitoring system 800 performs the ECG derivation, heart rate calculation, cardiac rhythm interpretation, CEB calculation, and trigger condition detection similarly to as described above for the mobile cardiac monitoring device 100 of FIG. 1, but for each of a plurality of patients. In another possible implementation, the central monitoring system 800 can communicate with one or more reader devices (e.g., reader device 710 of FIG. 7), which can derive a 15 or 22 lead ECG and can calculate CEB values for each patient. If a trigger is detected for any patient, the central monitoring system 800 provides an alert. For example, the central monitoring system can provide an audible alter (e.g., an alarm) as well as a visual alert (e.g. flashing lights) to indicate to a doctor which patient is associated with the detected trigger condition. The central monitoring system 800 can also send an alert message, such as a text message, telephone call, etc., to a device associated with a doctor. In another possible implementation, each of the mobile cardiac monitoring devices 802, 804, 806, 808, 810, and 812 can acquire 3-lead ECG voltage-time measurements, derive the full n-lead ECG, estimate the heart rate, and calculate the CEB for the respective patient, and then transmit the derived ECG, estimated heart rate, and calculated CEB for the respective to the central monitoring system 800 in real-time. The central monitoring system 800 then monitors the CEB of each patient to detect whether the trigger condition has occurred and generates the alert notification for a patient when the trigger condition is detected.

The central monitoring system 800 can be implemented on one or multiple computers using well-known computer processors, memory units, storage devices, computer software, and other components. A processor controls the overall operation of the central monitoring system 800 by executing computer program instructions which define such operation. The computer program instructions may be stored in a storage device (e.g., magnetic disk) and loaded into memory when execution of the computer program instructions is desired. For example, computer program instructions for performing the method steps of FIGS. 3, 5, and 6 can be stored in the memory and/or storage device and controlled by the processor executing the computer program instructions. The central monitoring system 800 includes one or more network interfaces for communicating with other devices, such as the mobile cardiac monitoring devices 802, 804, 806, 808, 810, and 812, via a network. The central monitoring system 800 also includes one or more displays for displaying the patient data of the various patients and for displaying alert notifications when a trigger condition is detected for a patient. The central monitoring system 800 also includes other input/output devices that enable user interaction with the central monitoring system 800 (e.g., keyboard, mouse, speakers, buttons, etc.).

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the described invention and that various modifications may be implemented by those skilled in the art without departing from the scope and spirit of the invention. Those skilled in the art could implement various other feature combinations without departing from the scope and spirit of the invention.

The invention claimed is:

1. A method for cardiac monitoring using a remote ambulatory cardiac monitoring device, comprising:
   storing a universal transformation matrix, the universal transformation matrix being generated by successively applying an abstract factor analysis and a simplex optimization algorithm to a training set of electrocardiogram voltage-time data arrays;
   receiving, at the remote ambulatory cardiac monitoring device, voltage-time measurements for a subset of electrocardiogram leads, the remote ambulatory cardiac monitoring device receiving the voltage-time measurements of a basis set of three orthogonal electrocardiogram leads from five electrodes in communication with the remote ambulatory cardiac monitoring device;

deriving a full set of electrocardiogram leads and voltage-time data thereof for an n-lead electrocardiogram for a user by applying the stored universal transformation matrix to the voltage-time measurements of the basis set of three orthogonal electrocardiogram leads;

determining a heart rate and monitoring a cardiac rhythm of the user based on the voltage-time measurements for at least one lead of the subset of electrocardiogram leads;

calculating first, second, and third eigenvalues for each heartbeat of the voltage-time data of the derived full set of electrocardiogram leads by constructing a covariance matrix from each said heartbeat of the voltage-time data of the derived full set of electrocardiogram leads;

determining a dynamic cardiac electrical biomarker for each said heartbeat based on each said calculated third eigenvalue, each said calculated third eigenvalue indicative of a measurement of dipolar activity of a cardiac electrical field, wherein the dynamic cardiac electrical biomarker quantifies dipolar and multipolar energy content in the cardiac electrical field continuously for each successive heartbeat over time from the derived full set of electrocardiogram leads, and wherein the more multipolar (the less dipolar) forces there are in the cardiac electrical field, the greater the potential for an acute myocardial injury;

detecting, at the remote ambulatory cardiac monitoring device, a trigger condition based on the determined dynamic cardiac electrical biomarker for each said heartbeat, wherein, the trigger condition is detected by detecting when a predetermined percentage, greater than a threshold, of said determined dynamic cardiac electrical biomarkers for each said heartbeat are in an abnormal zone within a predetermined time interval, the abnormal zone being indicative of the multipolar energy content in the cardiac electrical field;

transmitting, via a network, an alert from the remote ambulatory cardiac monitoring device to a predetermined remote device in response to detecting the trigger condition in real time; and allowing healthcare personnel to immediately initiate treatment protocols based on the detection of the trigger condition.

2. The method of claim 1, wherein deriving the full set of electrocardiogram leads, determining the heart rate, and determining the dynamic cardiac electrical biomarker are performed by the remote ambulatory cardiac monitoring device.

3. The method of claim 2, wherein transmitting the alert from the remote ambulatory cardiac monitoring device to the predetermined remote device in response to detecting the trigger condition comprises:

transmitting at least one of a text message and an email message including the derived full set of electrocardiogram leads, an estimated heart rate, and the determined dynamic cardiac electrical biomarker for a period of time preceding the trigger condition to the remote device.

4. The method of claim 2, wherein determining the dynamic cardiac electrical biomarker comprises:

determining a set of eigenvectors for each said heartbeat of the voltage-time data of the derived full set of electrocardiogram leads using abstract factor analysis; and determining the first, second, and third eigenvalues from the set of eigenvectors.

5. The method of claim 2, further comprising:

displaying a graph of the dynamic cardiac electrical biomarker for each said heartbeat over time on a display of the remote ambulatory cardiac monitoring device.

6. The method of claim 2, further comprising determining a static cardiac electrical biomarker from the derived full set of electrocardiogram leads by:

deriving an electrocardiogram in a predetermined time interval from the derived full set of electrocardiogram leads;

averaging a number of heartbeats in the derived electrocardiogram into a median beat; and calculating the static cardiac electrical biomarker for the predetermined time interval based on the median beat.

7. The method of claim 2, further comprising:

storing the derived full set of electrocardiogram leads, the determined heart rate, and the determined dynamic cardiac electrical biomarker on a removable storage of the remote ambulatory cardiac monitoring device.

8. The method of claim 2, further comprising:

displaying at least one of the voltage-time measurements for the subset of electrocardiogram leads, the derived full set of electrocardiogram leads, the determined heart rate and the determined dynamic cardiac electrical biomarker on a display of the remote ambulatory cardiac monitoring device.

9. The method of claim 2, further comprising:

transmitting the derived full set of electrocardiogram leads, the determined heart rate, and the determined dynamic cardiac electrical biomarker to the remote device in real time.

10. The method of claim 1, wherein receiving the voltage-time measurements of the basis set of three orthogonal electrocardiogram leads comprises:

receiving the voltage-time measurements of the basis set of three orthogonal electrocardiogram leads from the five electrodes in communication with the remote ambulatory cardiac monitoring device, wherein a ground is located within one of the electrodes that records the basis set of three orthogonal electrocardiogram leads.

11. The method of claim 1, wherein the n-lead electrocardiogram is a 12 lead electrocardiogram.

12. The method of claim 1, wherein the n-lead electrocardiogram is a 15 lead or a 22 lead electrocardiogram.

13. The method of claim 1, wherein receiving the voltage-time measurements of the basis set of three orthogonal electrocardiogram leads comprises:

receiving voltage-time measurements for I, aVF, and V2 electrocardiogram leads.

14. The method of claim 1, wherein receiving the voltage-time measurements of the basis set of three orthogonal electrocardiogram leads comprises:

receiving voltage-time measurements for I, II, and V2 electrocardiogram leads.

15. The method of claim 1, wherein determining the dynamic cardiac electrical biomarker from the derived full set of electrocardiogram leads comprises:

determining the dynamic cardiac electrical biomarker from 12 leads of the n-lead electrocardiogram.

16. The method of claim 1, wherein receiving, at the remote ambulatory cardiac monitoring device, voltage-time measurements for a subset of electrocardiogram leads of a user comprises:

receiving the voltage-time measurements for the subset of electrocardiogram leads from the five electrodes via a wireless communication protocol.

17. A remote ambulatory cardiac monitoring device comprising:
a storage device for storing a universal transformation matrix, the universal transformation matrix being generated by successively applying an abstract factor analysis and a simplex optimization algorithm to a training set of electrocardiogram voltage-time data arrays;
five electrocardiogram (ECG) electrodes for acquiring voltage-time measurements for a subset of ECG leads by acquiring voltage-time measurements of a basis set of three orthogonal ECG leads from the five electrodes in communication with the remote ambulatory cardiac monitoring device;
an ECG derivation module for deriving a full set of ECG leads and voltage-time data thereof for an n-lead ECG for a user by applying the stored universal transformation matrix to the voltage-time measurements of the basis set of three orthogonal electrocardiogram leads;
a heart rate calculation and cardiac rhythm monitoring module for determining a heart rate and monitoring a cardiac rhythm of the user based on the acquired voltage-time measurements for at least one lead of the subset of ECG leads;
a cardiac electrical biomarker (CEB) calculation module for
calculating first, second, and third eigenvalues for each heartbeat of the voltage-time data of the derived full set of electrocardiogram leads by constructing a covariance matrix from each said heartbeat of the voltage-time data of the derived full set of electrocardiogram leads;
determining a dynamic CEB for each said heartbeat based on each said calculated third eigenvalue, each said calculated third eigenvalue indicative of a measurement of dipolar activity of a cardiac electrical field, wherein the dynamic cardiac electrical biomarker quantifies dipolar and multipolar energy content in the cardiac electrical field continuously for each successive heartbeat over time from the derived full set of ECG leads, and wherein the more multipolar (the less dipolar) forces there are in the cardiac electrical field, the greater the potential for an acute myocardial injury; and
an alert module for
detecting, at the remote ambulatory cardiac monitoring device, a trigger condition based on the determined dynamic CEB for each said heartbeat, wherein the trigger condition is detected by detecting when a predetermined percentage, greater than a threshold, of said determined dynamic CEBs for each said heartbeat are in an abnormal zone within a predetermined time interval, the abnormal zone being indicative of the multipolar energy content in the cardiac electrical field, and
transmitting an alert, via a data network, from the remote ambulatory cardiac monitoring device to another remote device controlled by healthcare personnel in response to detecting the trigger condition in real time such that healthcare personnel may immediately initiate treatment protocols based on the detection of the trigger condition.

18. The remote ambulatory cardiac monitoring device of claim 17,
wherein the storage device stores the derived full set of ECG leads, an estimated heart rate, and the determined dynamic CEB for the user.

19. The remote ambulatory cardiac monitoring device of claim 17, further comprising:
a display for displaying the derived full set of ECG leads, an estimated heart rate, and the determined dynamic CEB for the user.

20. The remote ambulatory cardiac monitoring device of claim 19, wherein the display displays a graph of the dynamic CEB over time.

21. The remote ambulatory cardiac monitoring device of claim 17, further comprising:
a network interface for transmitting the derived full set of ECG leads, an estimated heart rate, and the determined dynamic CEB to a remote device.

22. The remote ambulatory cardiac monitoring device of claim 17, wherein the ECG electrodes comprise a left arm electrode, a right arm electrode, a left leg electrode, a right leg electrode, and a V2 electrode.

23. The remote ambulatory cardiac monitoring device of claim 17, further comprising:
a removable storage device for storing the derived full set of ECG leads, an estimated heart rate, and the determined dynamic CEB for the user.

24. The remote ambulatory cardiac monitoring device of claim 17, wherein the ECG electrodes transmit the acquired voltage-time measurements for the subset of ECG leads via a wireless communication protocol.

25. A remote ambulatory cardiac monitoring device, comprising:
a hardware processor; and
a memory storing computer program instructions, which when executed by the hardware processor causes the hardware processor to perform operations comprising:
deriving a full set of electrocardiogram (ECG) leads and voltage-time data thereof for an n-lead ECG for a user by applying a universal transformation matrix to voltage-time measurements of a basis set of three orthogonal ECG leads, the universal transformation matrix being generated by successively applying an abstract factor analysis and a simplex optimization algorithm to a training set of ECG voltage-time data arrays and the voltage-time measurements of the basis set of three orthogonal ECG leads being received from five ECG electrodes in communication with the remote ambulatory cardiac monitoring device;
determining a heart rate and monitoring a cardiac rhythm of the user based on the voltage-time measurements for at least one lead of the subset of ECG leads;
calculating first, second, and third eigenvalues for each heartbeat of the voltage-time data of the derived full set of ECG leads by constructing a covariance matrix from each said heartbeat of the voltage-time data of the derived full set of ECG leads;
determining a dynamic cardiac electrical biomarker (CEB) for each said heartbeat based on each said calculated third eigenvalue, each said calculated third eigenvalue indicative of a measurement of dipolar activity of a cardiac electrical field, wherein the dynamic CEB quantifies dipolar and multipolar energy content in the cardiac electrical field continuously for each successive heartbeat over time from the derived full set of ECG leads, and wherein the more multipolar (the less dipolar) forces there are in the cardiac electrical field, the greater the potential for an acute myocardial injury;

detecting a trigger condition based on the determined dynamic CEB for each said heartbeat, wherein the trigger condition is detected by detecting when a predetermined percentage, greater than a threshold, of said determined dynamic CEBs for each said heartbeat are in an abnormal zone within a predetermined time interval, the abnormal zone being indicative of the multipolar energy content in the cardiac electrical field; and transmitting, via a network, an alert from the remote ambulatory cardiac monitoring device to a predetermined remote device in response to detecting the trigger condition in real time such that healthcare personnel may immediately initiate treatment protocols based on the detection of the trigger condition.

26. The remote ambulatory cardiac monitoring device of claim 25, wherein the n-lead ECG is a 12 lead ECG.

27. The remote ambulatory cardiac monitoring device of claim 25, wherein the n-lead ECG is a 22 lead or 15 lead ECG.

28. The remote ambulatory cardiac monitoring device of claim 25, wherein determining the dynamic CEB comprises:
determining a set of eigenvectors for each said heartbeat of the voltage-time data of the derived full set of electrocardiogram leads using abstract factor analysis; and
determining the first, second, and third eigenvalues from the set of eigenvectors.

29. The remote ambulatory cardiac monitoring device of claim 25, further comprising:
a display for displaying the derived full set of ECG leads, the determined heart rate, and the determined dynamic CEB.

30. The remote ambulatory cardiac monitoring device of claim 25, further comprising
a removable storage device for storing the derived full set of ECG leads, the determined heart rate, and the determined dynamic CEB for the user.

31. The remote ambulatory cardiac monitoring device of claim 25, further comprising:
a network interface for transmitting the derived full set of ECG leads, the determined heart rate, and the determined dynamic CEB for the user to the remote device via the network.

32. A system for cardiac monitoring of a plurality of patients, comprising:
a plurality of remote ambulatory cardiac monitoring devices, wherein each remote ambulatory cardiac monitoring device
acquires voltage-time measurements for a subset of electrocardiogram (ECG) leads of a respective one of a plurality of patients, the voltage-time measurements being of a basis set of three orthogonal ECG leads from five electrodes in communication with the respective remote ambulatory cardiac monitoring device, and
transmits the voltage-time measurements for the subset of ECG leads, including the basis set of three orthogonal ECG leads, of the respective one of a plurality of patients via a network; and
a central monitoring system for
receiving the voltage-time measurements for the subset of ECG leads for each of the plurality of patients transmitted from the plurality of remote ambulatory cardiac monitoring devices,
deriving a respective full set of ECG leads and voltage-time data thereof for each of the plurality of patients from the respective subset of ECG leads by applying a stored universal transformation matrix to the voltage-time measurements of the basis set of three orthogonal ECG leads,
calculating first, second, and third eigenvalues for each heartbeat of the voltage-time data for a respective derived full set of ECG leads by constructing a covariance matrix from each said heartbeat of the voltage-time data of the respective derived full set of ECG leads,
calculating a respective dynamic cardiac electrical biomarker (CEB) for each said heartbeat based on each said calculated third eigenvalue for each of the plurality of patients, each said calculated third eigenvalue being indicative of a measurement of dipolar activity of a cardiac electrical field and the respective dynamic CEB quantifying dipolar and multipolar energy content in the cardiac electrical field continuously for each successive heartbeat over time from the respective derived full set of ECG leads, and
detecting whether a trigger condition occurs for each of the plurality of patients based on the calculated respective dynamic CEB for each said heartbeat calculated for each of the plurality of patients, wherein the trigger condition is detected by detecting when a predetermined percentage, greater than a threshold, of the calculated respective dynamic CEBs for each said heartbeat are in an abnormal zone within a predetermined time interval, the abnormal zone being indicative of the multipolar energy content in the cardiac electrical field, wherein the central monitoring system generates at least one of an audio alert or a visual alert that indicates for which patient the trigger condition has occurred in response to detecting that a trigger condition has occurred for one of the plurality of patients.

33. The system of claim 32, wherein the central monitoring system comprises one or more displays for displaying the respective derived full set of ECG leads and the respective calculated CEB for each of the plurality of patients.

34. The system of claim 32, wherein each of the plurality of cardiac monitoring devices acquires voltage-time measurements for 3 ECG leads of the respective one of a plurality of patients, and the central monitoring system derives a respective full set of ECG leads for a 12 lead ECG from the voltage-time measurements for the 3 ECG leads for each of the plurality of patients.

35. A method for cardiac monitoring comprising:
acquiring, by a remote ambulatory cardiac monitoring device, voltage-time measurements for a subset of electrocardiogram (ECG) leads, the remote ambulatory cardiac monitoring device acquiring the voltage-time measurements of a basis set of three orthogonal ECG leads from five ECG electrodes in communication with the remote ambulatory cardiac monitoring device,
transmitting, via a network, the voltage-time measurements for the subset of ECG leads, including the basis set of three orthogonal ECG leads, to a remote monitoring center in real time,
receiving, by the remote monitoring center, the voltage-time measurements for the subset of ECG leads,
deriving, by the remote monitoring center, a full set of ECG leads and voltage-time data thereof for an n-lead ECG for a user by applying a stored universal transformation matrix to the voltage-time measurements of the basis set of three orthogonal ECG leads, determining, by the remote monitoring center, a heart rate and monitoring a cardiac rhythm of the user based on the voltage-time measurements for at least one lead of the subset of ECG leads, calculating, first, second, and third eigenvalues for each heartbeat of the voltage-time data of the derived full set of ECG leads by constructing a covariance matrix from each said heartbeat of the voltage-time data of the derived full set of ECG leads, determining, by the remote monitoring center, a dynamic cardiac electrical biomarker (CEB) for each said heartbeat based on each said calculated third eigenvalue, each said calculated third eigenvalue indicative of a measurement of dipolar activity of a cardiac electrical field, wherein the dynamic CEB quantifies dipolar and multipolar energy content in the cardiac electrical field continuously for each successive heartbeat over time from the derived full set of ECG leads, and wherein the more multipolar (the less dipolar) forces there are in the cardiac electrical field, the greater the potential for an acute myocardial injury, detecting, by the remote monitoring center, a trigger condition based on the determined dynamic CEB for each said heartbeat, wherein the trigger condition is detected by detecting when a predetermined percentage, greater than a threshold, of said determined dynamic CEBs for each said heartbeat being in an abnormal zone within a predetermined time interval, the abnormal zone being indicative of the multipolar energy content in the cardiac electrical field, and generating, by the remote monitoring center, an alert in response to detecting the trigger condition in real time such that healthcare personnel may immediately initiate treatment protocols based on the detection of the trigger condition.

* * * * *